(12) United States Patent
Gupton

(10) Patent No.: US 6,399,781 B1
(45) Date of Patent: Jun. 4, 2002

(54) PROCESS FOR MAKING 3-AMINO-2-CHLORO-4-METHYLPYRIDINE

(75) Inventor: Bernard Franklin Gupton, Midlothian, VA (US)

(73) Assignee: Boehringer Ingelheim Chemicals, Inc., Petersburg, VA (US)

(*) Notice: Subject to any disclaimer, the term of this patent is extended or adjusted under 35 U.S.C. 154(b) by 0 days.

(21) Appl. No.: 09/950,727

(22) Filed: Sep. 12, 2001

Related U.S. Application Data

(60) Provisional application No. 60/291,841, filed on May 17, 2001, and provisional application No. 60/239,300, filed on Oct. 10, 2000.

(51) Int. Cl.[7] ............................................. C07D 213/73
(52) U.S. Cl. ........................................ 546/311; 558/453
(58) Field of Search ............................ 546/311; 558/453

(56) References Cited

U.S. PATENT DOCUMENTS

| | | | |
|---|---|---|---|
| 5,200,522 A | 4/1993 | Grozinger et al. | 546/250 |
| 5,366,972 A | 11/1994 | Hargrave et al. | 514/220 |
| 5,569,760 A | 10/1996 | Schneider et al. | 540/495 |
| 5,654,429 A | 8/1997 | Nummy | 546/21 |
| 5,668,287 A | 9/1997 | Grozinger et al. | 546/250 |
| 5,686,618 A | 11/1997 | Schneider | 546/311 |

FOREIGN PATENT DOCUMENTS

| | | |
|---|---|---|
| WO | WO86 01815 A1 | 3/1986 |
| WO | WO00 43364 A1 | 7/2000 |
| WO | WO00 43365 A1 | 7/2000 |

OTHER PUBLICATIONS

Baldwin, J.J., et al; "Utilization of Beta, Gamma–Unsaturated Aldehyde Equivalents in the Synthesis of Substituted 2–Halonicotinic Acid Derivatives", J. Org. Chem. vol. 43, No. 12, 1978, pp. 2529–2535.

Chapman, et al; "Pyrazolopyridines. Part 5.1 Preparation and Reactions of Pyrazolo–[3,4–c]pyridines", J.C.S. Perkin, pp. 2398–2404, 1980.

Grozinger et al; "Synthesis of Nevirapine and its Major Metabliite", Heterocyclic Chem. 32, 259 (1995).

Hargrave, et al; "Novel Non–Nucleoside Inhibitors of HIV–1 Reverse Transcriptase. 1. Tricyclic Pyridobenzo–and Dipyridodiazepinones", J. Med. Chem, 1991, 34, 2231–2241.

Zhang, et al; "Regioselective Synthesis of 2–Chloro–3–Pyridinecarboxylates"; Tetrahedron vol. 51, No. 48, pp. 13177–13184, 1995.

*Primary Examiner*—Zinna Northington Davis
(74) *Attorney, Agent, or Firm*—Robert P. Raymond; Alan R. Stempel; Mary-Ellen M. Devlin

(57) ABSTRACT

A method for making 3-amino-2-chloro-4-methylpyridine, as shown in Scheme 12, below.

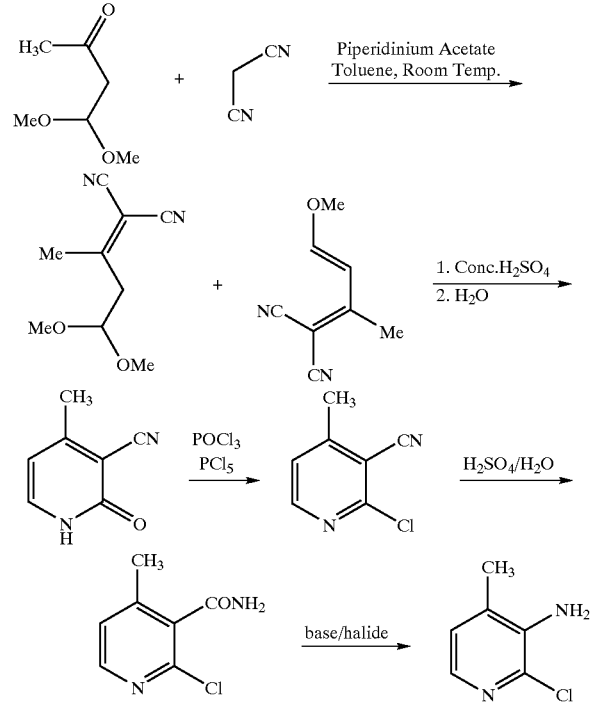

11 Claims, No Drawings

PROCESS FOR MAKING 3-AMINO-2-CHLORO-4-METHYLPYRIDINE

RELATED APPLICATIONS

Benefit of U.S. Provisional Application Serial No. 60/239,300, filed on Oct. 10, 2000 and U.S. Provisional Application Serial No. 60/291,841, filed on May 17, 2001 are hereby claimed.

FIELD OF THE INVENTION

The invention relates to an improved process for making 3-amino-2-chloro-4-methylpyridine, also known as CAPIC.

BACKGROUND OF THE INVENTION

CAPIC is a key intermediate in the production of nevirapine, a non-nucleosidic reverse transcriptase inhibitor that has been established to be clinically useful for the treatment of infection by HIV-1.

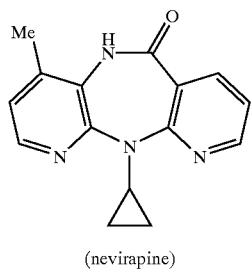

(nevirapine)

Syntheses of nevirapine from CAPIC have been described by Hargrave et al., in *J. Med. Chem.* 34, 2231 (1991) and U.S. Pat. No. 5,366,972, and by Schneider et al., in U.S. Pat. No. 5,569,760.

Several processes for preparing CAPIC have been described in the literature. It is believed that the earliest synthesis of CAPIC, depicted below in Scheme 1, is that of Chapman et al. (*J. Chem Soc.Perkin Trans.*1, (1980), 2398–2404).

Scheme 1

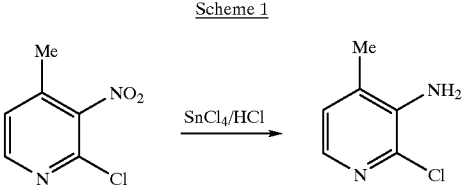

A closely related synthesis for CAPIC, depicted below in Scheme 2, has been described by Hargrave et al. (U.S. Pat. No. 5,366,972).

Scheme 2

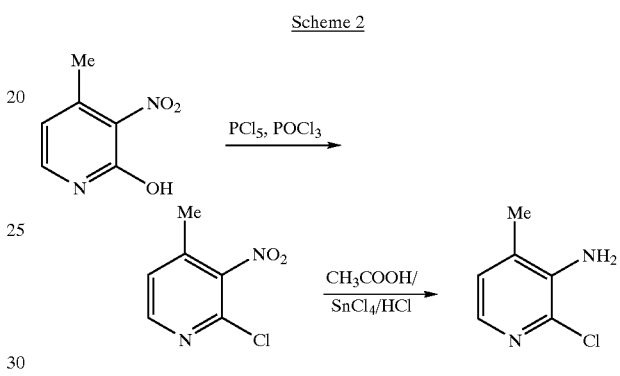

As reported by Grozinger et al. (*J. Heterocyclic Chem.*, 32, 259 (1995)), CAPIC has been synthesized in small laboratory batches by nitrating the readily available 2-amino-4-picoline or 2-hydroxy-4-picoline, as depicted below in Scheme 3. This procedure suffers from non-selective nitration at positions 3 and 5, as well as thermochemical hazards and potential for "run-away" when carried out in large quantities.

Scheme 3

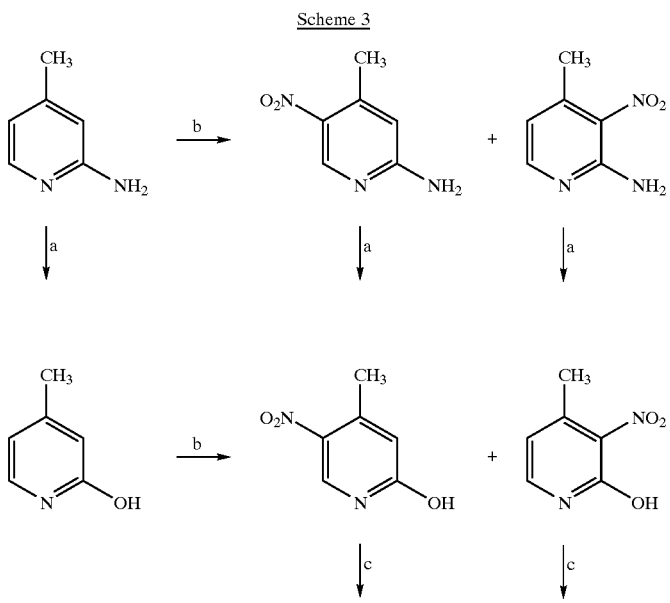

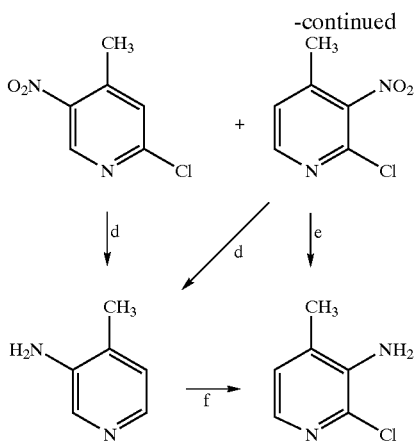

a) = NaNO₂/HCl
b) = H2SO₄/HNO₃
c) = POCl₃/PCl₅
d) = 10% Pd/C/H₂
e) = Raney Ni/H₂ or
   5% Rh/C/H₂ or
   SnCl₂/H₂O/HCl
f) = HCl/Cl₂

The drawbacks of the nitration-based process lead Grozinger to develop the two synthetic routes, which start from ethylacetoacetone and cyanacetamide, that are described in U.S. Pat. Nos. 5,668,287 and are depicted below in Schemes 4 and 5. Both of the latter two synthetic routs require the dichlorination of the intermediate 2,6-dihydroxy-2 and 6, subsequent de-chlorination and finally selective re-chorination, using chlorine gas, at position 2. The di-chlorination and dehalogenation, as well as the selective monochlorination at position 2 require special manufaturing equipment that is expensive and may not be readily available.

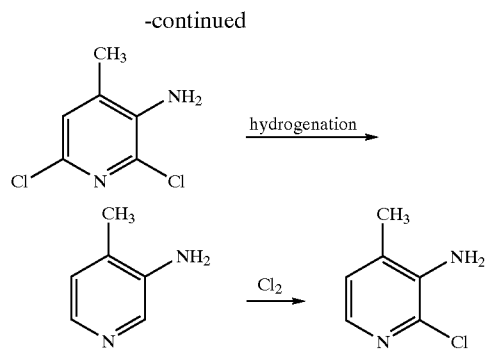

Scheme 4

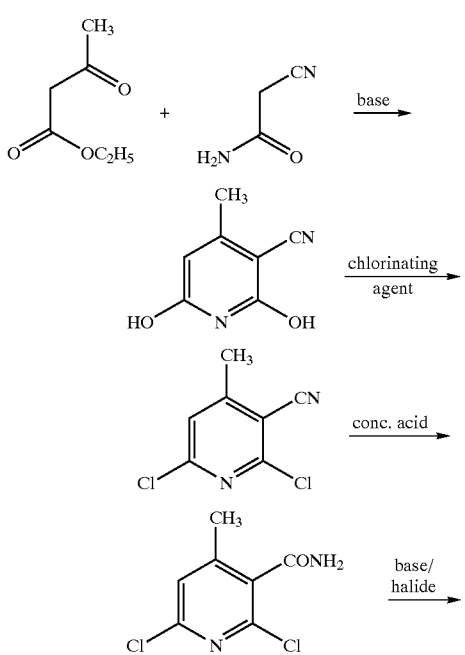

Scheme 5

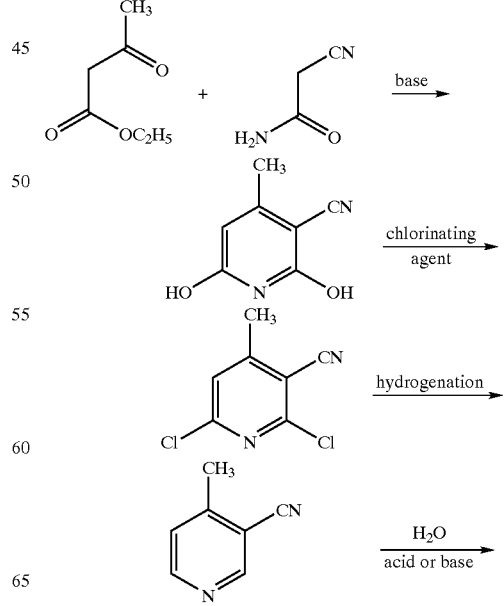

-continued

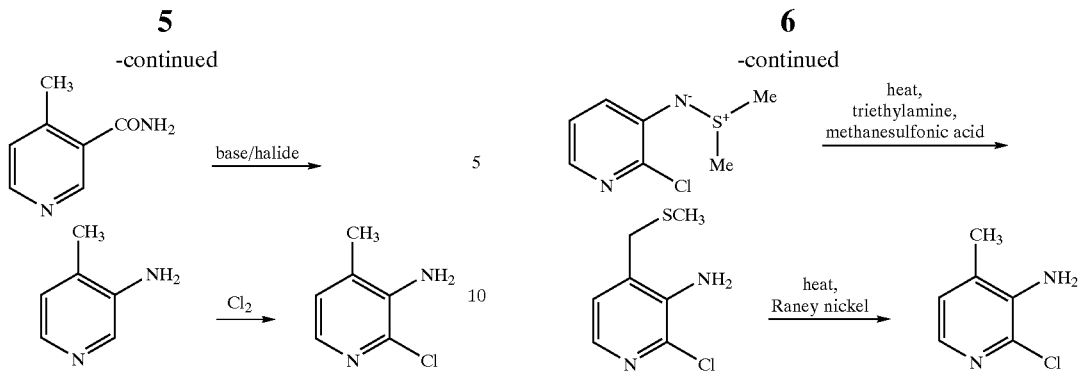

Schneider (U.S. Pat. No. 5,686,618) has provided an alternative means for mono-chlorinating 3-amino-4-methylpyridine at position 2, using $H_2O_2$ in HCl, instead of chlorine gas.

Yet another synthesis, depicted below in Scheme 6, comprising the steps of chlorination of ethyl cyanoacetate, Michael addition with crotonaldehyde, cyclization, conversion to the amide and finally reduction to the amine has been described by Zhang et al. (*Tetrahedron* 51(48), 13177–13184 (1995)), who report that while the desired product was obtained, the Michael addition was slow and the cyclization low-yielding.

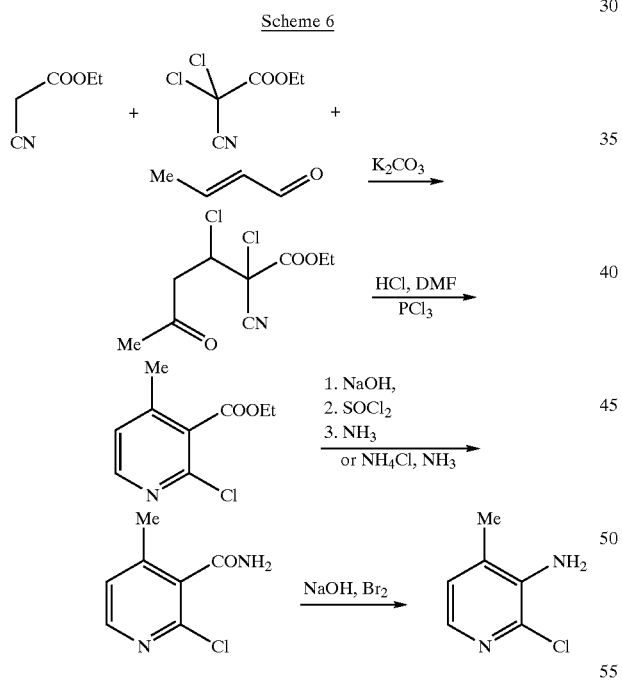

A synthesis beginning with 2-chloro-3-aminopyridine has been disclosed by Nummy (U.S. Pat. No. 5,654,429). This is depicted below in Scheme 7.

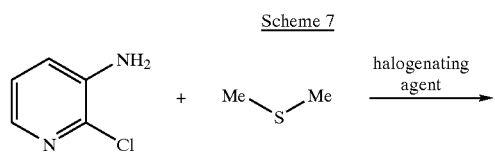

International Application WO 00/43365 describes the process for preparing CAPIC that is depicted below in Scheme 8.

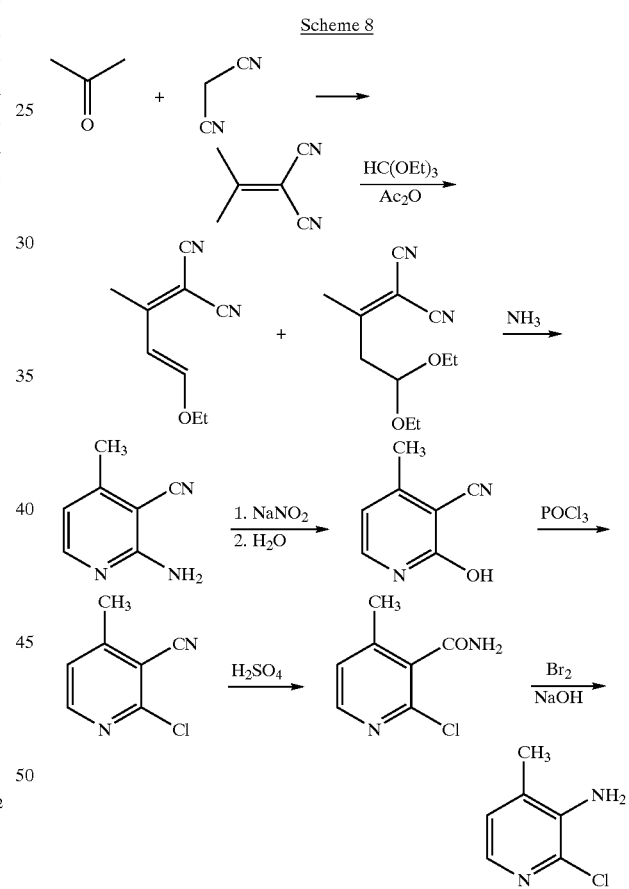

A closely related alternative, depicted below in Scheme 9, is disclosed in International Application PCT/US00/00261.

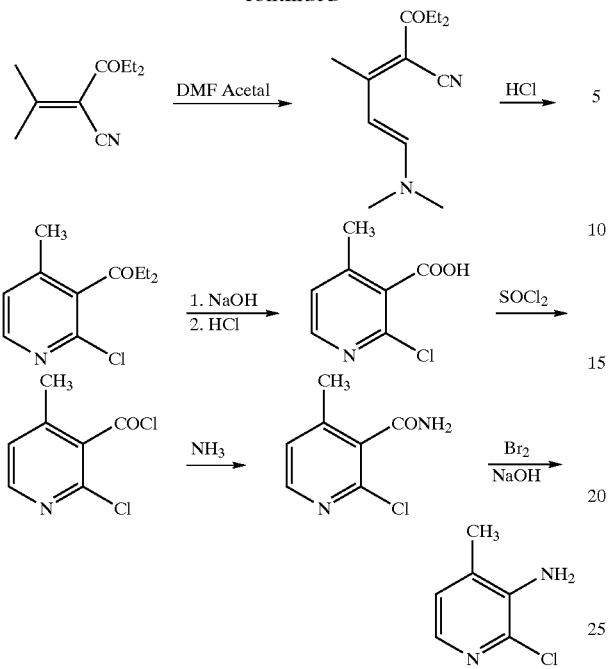
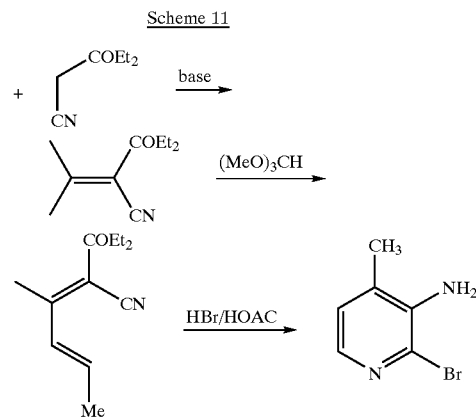

Baldwin et al. (*J. Org. Chem.*, 43, 2529 (1978)), reported a method for the preparation of 2-halonicotinic acid derivatives using β,γ-unsaturated aldehyde equivalents as shown in Scheme 10. The procedure involves the initial Knovenagel condensation of an aldehyde or ketone with ethyl cyanoacetate or malonitrile followed by reaction with DMF acetal. The cyclization of the β,γ-unsaturated aldehyde equivalent is carried out by treatment with HBr-acetic acid to give the 2-bromo adduct directly. Reaction yields with DMF acetal were in the 5 to 60% range, depending on the nature of the alkyl substituents. In several cases, the reaction of DMF acetal with the Knovenagel adduct led to dimer formation. Overall yields for the two step process varied from 3 to 35% depending on the nature of the substituents.

Scheme 10

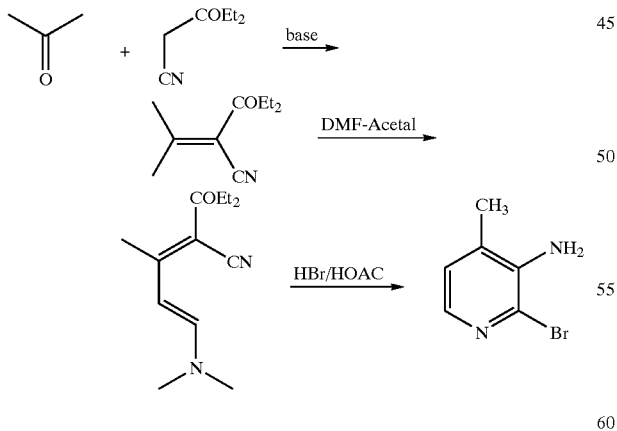

Baldwin et al., supra., also used mixtures of acetals and enol ethers as β,γ-unsaturated aldehyde equivalents to overcome the limitations associated with the use of DMF acetal in the preparation of 2-bromonicotinic acid derivatives (Scheme 11). Yields also tended to vary with this approach depending on the substitution pattern of Knovenagel adduct. Yields for the cyclization step ranged from 29 to 74% while overall yields for the two step process ranged from 15 to 40%.

In summary, the methods that have been developed to date for the preparation of CAPIC and other related 4-alkylnicotinic acid derivatives suffer from excessive complexity, inefficiency and/or lack of regiocontrol. Of the approaches considered, Baldwin's use of acetal/enol ether systems addresses the regioselectivity issues most effectively

DESCRIPTION OF THE INVENTION

In its most general aspect, the invention comprises an improved process for the preparation of 2-chloro-3-amino-4-methylpyridine (CAPIC) which comprises the following steps:

(a) reacting acetylacetaldehyde dimethyl acetal

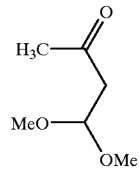

with malononitrile

to yield a mixture of 4,4-dicyano-3-methyl-3-butenal dimethyl acetal and 1,1-dicyano-4-methoxy-2-methyl-1,3-butadiene

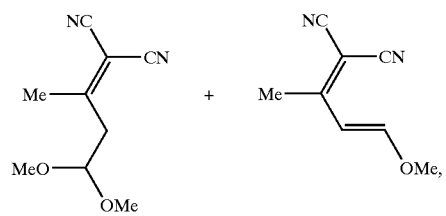

(b) treating the mixture of 4,4-dicyano-3-methyl-3-butenal dimethyl acetal and 1,1-dicyano-4-methoxy-2- methyl-1,3-butadiene so produced with a strong acid and water, to yield 3-cyano-4-methyl-2-pyridone

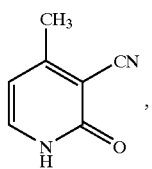

(c) treating the 3-cyano-4-methyl-2-pyridone so produced with a strong chlorinating agent, to yield 3-cyano-2-chloro-4-methylpyridine

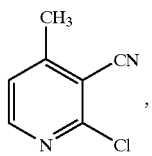

(d) treating the 3-cyano-2-chloro-4-methylpyridine produced in the preceding step with a strong acid and water, to yield 2-chloro-3-amido-4-methylpyridine

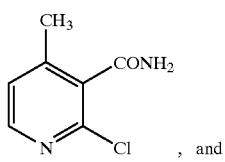, and (e) treating the 2-chloro-3-amido-4-methylpyridine produced in the preceding step with a strong base and a halide, to yield 2-chloro-3-amino-4-methylpyridine.

This general method is depicted below in Scheme 12.

Scheme 12

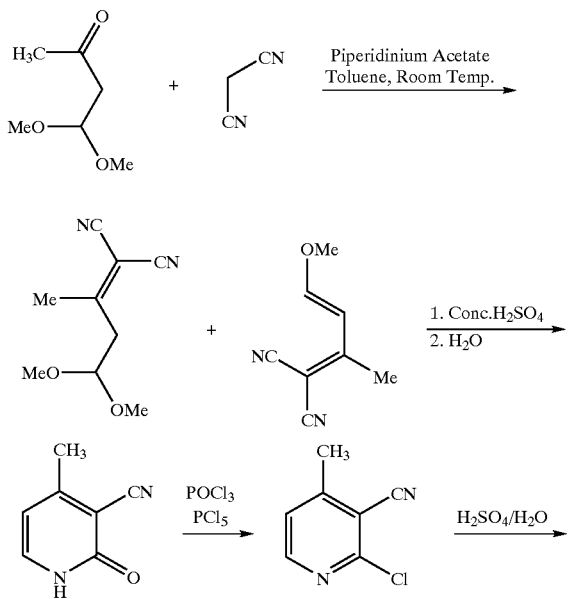

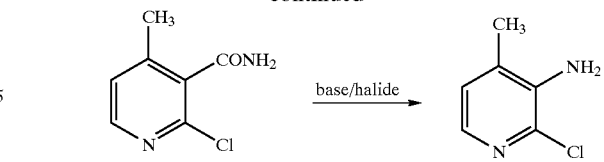

The intermediates 4,4-dicyano-3-methyl-3-butenal dimethyl acetal and 1,1-dicyano-4-methoxy-2-methyl-1,3-butadiene are believed to be novel, and constitute an aspect of the invention.

The first step of the above-described process is a Knovenagel condensation. This is carried out in an organic solvent at a temperature in the range between 0 and 50° C. Acceptable solvents are, for example, aromatic hydrocarbons such as benzene, toluene or alkanols such as methanol, ethanol, propanols and other higher molecular weight alcohols. The preferred solvents are toluene and methanol. The preferred reaction temperature is 15 to 25° C. The condensation is run in the presence of a small quantity of an ammonium salt catalyst. Preferred catalysts are heterocyclic ammonium salts. Most preferred is piperidinium acetate.

The product of the Knovenagel condensation is a mixture of 4,4-dicyano-3-methyl-3-butenal dimethyl acetal and 1,1-dicyano-4-methoxy-2-methyl-1,3-butadiene. These two compounds need not be separated, as they both are converted in the next step, which is an acid-catalyzed cyclization, to 3-cyano-4-methyl-2-pyridone. It is possible to conduct the cyclization simply by acidifying the initial reaction mixture, without isolation of the mixture of intermediates. However, it is preferred to first isolate the two intermediates from the other components of the crude Knovenagel reaction mixture. This is conveniently accomplished by washing the reaction mixture emanating from the condensation with water, to remove the basic catalyst, followed by evaporation, to remove the solvent (toluene or methanol).

While the crude reaction mixture can be carried forward to the next step after catalyst removal and concentration, it has been discovered that this crude product contains undesired byproducts that tend to be carried forward into subsequent reaction steps and reduce yields. Therefore it is desirable to remove these byproducts once the catalyst removal and concentration have been completed. The removal of these byproducts can be performed by simple distillation techniques, preferably by continuous short path distillation such as wiped or thin film evaporation. This technique is particularly effective for the removal of high boiling materials, which appears to be sufficient to obtain the observed yield improvements.

The acid-catalyzed cyclization is performed with a strong acid, such as, for example, concentrated and sulfuric acid. As the reaction is highly exothermic, it is best to introduce the mixture of 4,4-dicyano-3-methyl-3-butenal dimethyl acetal and 1,1-dicyano-4-methoxy-2-methyl-1,3-butadiene into the acid slowly, and with stirring, so that the temperature of the mixture does not rise above about 50° C. After evolution of heat has substantially ceased, the reaction mixture is heated to between about 30 and 50° C. preferably 50° C. and held at that temperature for between about 1 and 3 hours, preferably about 1.5 hours, to complete the reaction. The reaction mixture is cooled to ambient temperature, water is added, and the intermediate product, 3-cyano-4-methyl-2-pyridone, is filtered off, washed with water and dried.

Next, the 3-cyano-4-methyl-2-pyridone so produced is treated with a strong chlorinating agent. Suitable chlorinating agents are SOCl₂, POCl₃ and PCl₅. It is preferred to use POCl₃ (10 parts) and PCl₅ (1 part). The reaction mixture is heated to reflux (approximately 115° C.) and held under this condition for about two hours, or until the chlorination is essentially complete. The chlorinating agent is removed. For example, excess POCl₃ may be removed by distillation. The reaction mixture is then cooled and water is added. The 2-chloro-3-cyano-4-methylpyridine is filtered from the aqueous mixture. The aqueous filtrate is extracted with an inert organic solvent such as chloroformn, methylene chloride, with methylene chloride being preferred in order to recover the residual 2-chloro-3-cyano-4-methylpyridine.

The 3-cyano intermediate is next converted to a 3-amido compound. This is accomplished by treating the cyano intermediate with a concentrated, aqueous strong acid, such as sulfuric acid. This is preferably done with stirring, at a temperature between about 70 and 110° C. preferably at about 90° C. The mixture was heated to between about 80 and 120° C., preferably about 100° C. and held at that temperature for three hours, or until further reaction ceases. The reaction mixture is then cooled to between about 70 and 110° C. preferably about 90° C. and water is added. The mixture is then cooled to between about 0 and 20° C. preferably about 10° C. and held at that temperature for about one hour. The solid product, 2-chloro-3-amido-4-methylpyridine, is isolated from the reaction mixture by filtration, washed with water and dried.

In the final step of the process, the 3-amido intermediate is converted to the 3-amino final product by adding it to a mixture of a strong base and a halogen. The base may be aqueous sodium carbonate or sodium hydroxide, preferably sodium hydroxide. The halogen may be chlorine or bromine, preferably bromine. The resulting reaction mixture is heated to between about 10 and 30° C. preferably to about 22° C. Water is then added to the reaction mixture followed by heating to between 60 and 80° C. preferably to about 70° C. for one additional hour. The reaction mixture is cooled to ambient temperature and extracted with an inert organic solvent, such as chloroform or methylene chloride, preferably methylene chloride. The organic solvent is removed by evaporation, to yield 2-chloro-3-amino-4-methylpyridine.

Example 1, below, describes a specific preparation of CAPIC that was carried out in accordance with the general method of the invention.

EXAMPLE 1 a) Preparation of a Mixture of 4,4-Dicyano-3-methyl-3-butenal Dimethyl Acetal and 1,1-Dicyano-4-methoxy-2-methyl-1,3-butadiene (Knovenagel Condensation)

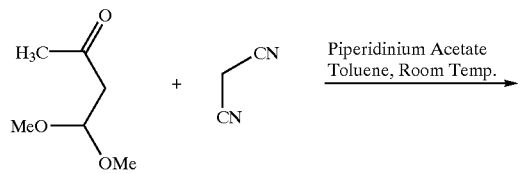

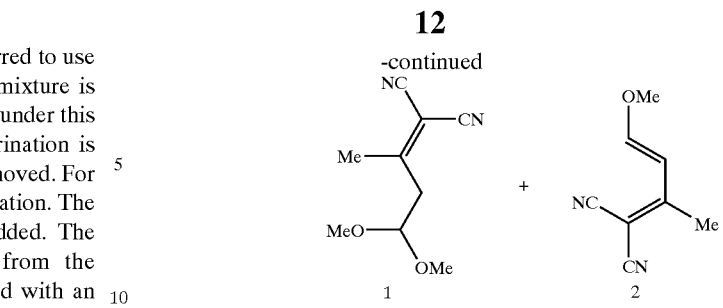

Piperidinium acetate (5.42 g, 0.037 moles) was added to a stirred solution of toluene (150 ml) and acetylacetaldehyde dimethyl acetal (49.3 g, 0.373 moles). Malononitrile (24.65 g, 0.373 moles) was then added to the reaction mixture over a 20-minute period. The mixture was allowed to stir for 24 hours at room temperature. The reaction mixture was then washed with 50 mL of water followed by rotary evaporation to give 67.14 g of a mixture of 4,4-dicyano-3-methyl-3-butenal dimethyl acetatal (1) and 1,1-dicyano-4-methoxy-2-methyl-1,3-butadiene (2).

mp: not isolated; Yield: 71.9% (1) and 21.6% (2); ¹H NMR: s 4.55 (m, 1H), 3.4 (5, 6H), 2.9 (d, 2H), 2.25 (5, 3H); IR (KBr): 3059, 2219, 1629, 1547, 1359, 1248, 1143, 981 cm⁻¹; Mass spectrum m/z: (1) m/z 179, 149, 121, 75 (2) 148, 133, 119, 91, 83, 78; Purity: crude mixture.

(b) Preparation of 3-Cyano-4-methyl-2-pyridone (Cyclization)

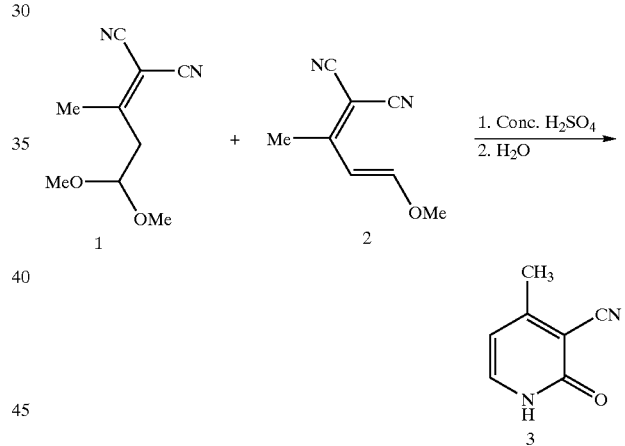

The mixture of 4,4-dicyano-3-methyl-3-butenal dimethyl acetatal (1) and 1,1-dicyano-4-methoxy-2-methyl-1,3-butadiene (2) produced by the preceding step was added to a stirred solution of concentrated sulfuric acid (109.8 g, 1.12 moles) at a rate so that the reaction contents did not exceed 30° C. The reaction mixture was then heated to 50° C. and held at that temperature for 1.5 hours. The reaction mixture was cooled to ambient temperature followed by the addition of water (150 mL). The product was filtered from the reaction mixture, washed with water (20 mL) and dried in a vacuum oven at 70° C. and full vacuum for 12 hours to give 40.7 g of 3-cyano-4-methyl-2-pyridone (3).

mp: 230–232° C. Yield: 81.4%; ¹H NMR:6.95 (d, J=2Hz, 1H), 6.29 (d, J=2Hz, 1H), 2.35(s, 3H); ¹³C NMR 162.0, 160.4, 140.0, 116.1, 108.1, 103.4,21.1; IR (KBr): 3144, 3097, 2979, 2833, 2227, 1652, 1635, 1616, 1539, 1484, 1242, 1218, 1173, 819 cm⁻¹; Mass spectrum m/z: 134, 105, 78, 63, 51; Purity: 98.6% by HPLC analysis (peak area basis);

(c) Preparation of 2-Chloro-3-cyano-4-methylpyridine (Chlorination)

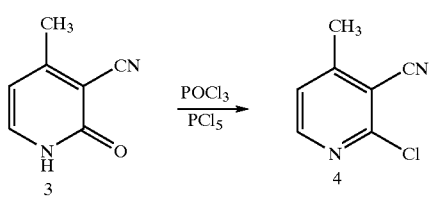

The product of the preceding step, 4-methyl-3-cyano-2-pyridone (40.7 g, 0.304 moles) was added to a stirred solution of POCL$_3$ (140 g, 0.912 moles) and PCl$_5$ (19.0 g, 0.091 moles). The reaction was heated to reflux (approximately 115° C.) and held under those conditions for two hours. Excess POCL$_3$ was removed by distillation. The reaction mixture was then cooled followed by the addition of water (30 mL) water. The aqueous mixture was extracted with 30 mL methylene chloride. The extracts were concentrated and 43.2 g was recovered as a tan solid, which was determined to be 2-chloro-3-cyano-4-methylpyridine (4).

mp: 102–104° C. Yield: 82.7%; $^1$H NMR: 8.03, (d, J=2 Hz, 1H), 7.6 (d, J=2 Hz, 1H), 2.5 (s, 3H); $^{13}$C NMR 156.1, 152.6, 151.8, 124.9, 114.4, 111.8, 20.6; Mass spectrum m/z: 155, 154, 152, 117, 116, 90, 89, 76, 64, 63, 62; FTIR (KBr): 3144, 2979, 2834, 2228, 1653, 1616, 1540, 1484, 1242, 1218, 1173, 819, 607 cm$^{-1}$; Purity: 98.2% by HPLC analysis (peak area basis).

(d) Preparation of 2-Chloro-3-amido-4-methylpyridine (Addition of Water)

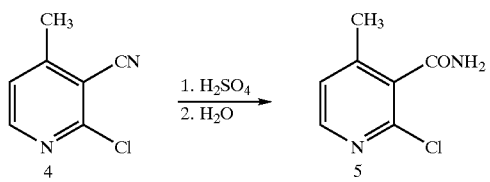

The product of the preceding step, 2-chloro-3-cyano-4-methylpyridine (34.14 g, 0.224 moles) was added to a stirred solution of concentrated sulfuric acid (65.87 g, 0.672 moles) at 90° C. The mixture was then heated to 100° C. and held at that temperature for three hours. The reaction was then cooled to 90° C. followed by the addition of water (121 mL). The mixture was cooled to 10° C. and held at that temperature for one hour. The solid product was isolated from the reaction mixture by filtration, washed with water (16 mL) and dried at 70° C. under full vacuum to give 34.7 g of 2-chloro-3-amido-4-methylpyridine (5).

mp: 178–179° C.; Yield: (90.9%; $^1$H NMR: 8.28 (d, J=8 Hz, 1H), 8.09 (s, 1H), 7.84 (s, 1H), 7.34 (d, J=8 Hz, 1H), 2.31 (s, 3H); $^{13}$C NMR: 166.4, 1149.0, 1437.8, 146.2, 136.0, 125.0, 18.9; Mass spectrum m/z: 155, 154, 152, 116, 91, 90, 89, 88, 76, 75, 64, 63, 62, 52, 51; FTIR (KBr): 3407, 3303, 3194, 3116, 3069, 3031, 2962, 2847, 1664, 1539, 1475, 1458, 1380, 1174, 1145, 798, 595 cm$^{-1}$.

(e) Preparation of 2-Chloro-3-amino-4-methylpyridine

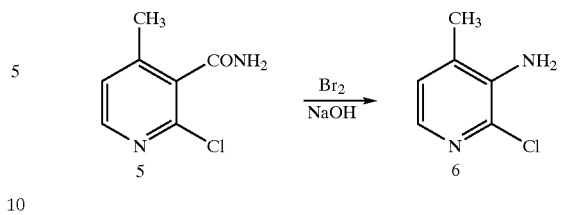

Bromine (34.7 g, 0.204 moles) was added to a stirred solution of sodium hydroxide (8.14 g. 0.224 moles) and water (205 mL) at 0° C. The product of the preceding step, 2-chloro-3-amido-4-picoline (34.7 g, 0.204 moles) was then added to the reaction mixture followed by heating to 22° C. An additional 66 mL water was then added to the reaction mixture followed by heating to 70° C. and stirring for one additional hour. The reaction mixture was cooled to ambient temperature and extracted with methylene chloride (60 mL). The methylene chloride was removed by rotary evaporation to give 24.8 g of 2-chloro-3-amino-4-methylpyridine (6).

mp: 69° C.; Yield: 85.2%; $^1$H NMR: 7.5 (d, J=4.64 Hz, 1H), 7.0 (d, J=4.28 Hz, 1H), 5.25 (s, 2H), 2.1 (s, 3H); $^{13}$C NMR: 140.0, 136.2, 135.6, 131.9, 125.7, 19.0; IR (KBr): 3429, 3308, 3198, 1630, 1590, 1550, 1475, 1451, 1441, 1418, 1377, 1295, 1122, 860, 821, 656, 527 cm$^{-1}$; Mass spectrum m/z: 145, 144, 142, 107, 106, 105, 80, 79, 78, 62, 54, 53, 52; Purity: 87.6%, HPLC analysis (peak area basis).

Example 2, below, describes a specific preparation of CAPIC that was carried out in accordance with the preferred method of the invention in which the Knovenagel condensation reaction product is purified by short path distillation.

a) Preparation of a Mixture of 4,4-Dicyano-3-methyl-3-butenal dimethyl Acetal and 1,1-Dicyano-4-methoxy-2-methyl-1,3-butadiene Followed by Short Path Distillation (Knovenagel Condensation)

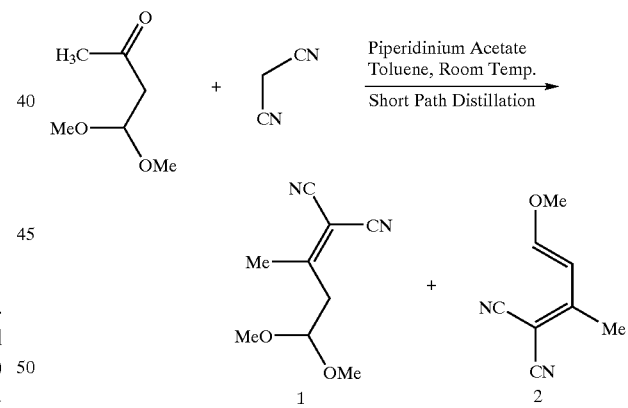

Piperidinium acetate (5.42 g, 0.037 moles) was added to a stirred solution of toluene (150 ml) and acetylacetaldehyde dimethyl acetal (49.3 g, 0.373 moles). Malononitrile (24.65 g, 0.373 moles) was then added to the reaction mixture over a 20-minute period. The mixture was allowed to stir for 24 hours at room temperature. The reaction mixture was then washed with 50 mL of water followed by rotary evaporation to give 67.14 g of a mixture of 4,4-dicyano-3-methyl-3-butenal dimethyl acetatal (1) and 1,1-dicyano-4-methoxy-2-methyl-1,3-butadiene (2). The crude reaction product was then distilled on a 0.1 square meter stainless steel wiped film evaporator at 109° C. 0.1 mm Hg and 240 RPM to give 60.1 kg of a yellow liquid Yield: 85.0% (1) and (2); $^1$H NMR: s 4.55 (m, 1H), 3.4 (5, 6H), 2.9 (d, 2H), 2.25 (5, 3H); IR(KBr): 3059, 2219, 1629, 1547, 1359, 1248, 1143, 981 cm⁻¹; Mass spectrum m/z: (1) m/z 179, 149, 121, 75 (2) 148, 133, 119, 91, 83, 78; Purity: 94.0% (1) and (2).

(b) Preparation of 3-Cyano-4-methyl-2-pyridone (Cyclization)

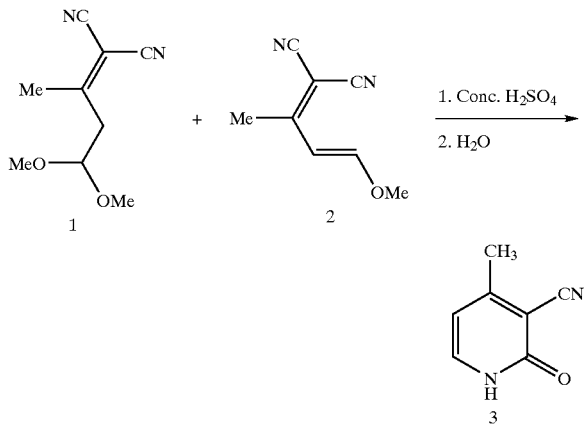

The mixture of 4,4-dicyano-3-methyl-3-butenal dimethyl acetatal (1) and 1, 1-dicyano-4-methoxy-2-methyl-1,3-butadiene (2) produced by the preceding step was added to a stirred solution of concentrated sulfuric acid (1 09.8 g, 1.12 moles) at a rate so that the reaction contents did not exceed 30° C. The reaction mixture was then heated to 50° C. and held at that temperature for 1.5 hours. The reaction mixture was cooled to ambient temperature followed by the addition of water (150 mL). The product was filtered from the reaction mixture, washed with water (20 mL) and dried in a vacuum oven at 70° C. and full vacuum for 12 hours to give 40.7 g of 3-cyano-4-methyl-2-pyridone (3).

mp: 230–232° C. Yield: 90.6%; ¹H NMR: 6.95 (d, J=2Hz, 1H), 6.29 (d, J=2Hz, 1H), 2.35(s, 3H); ¹³C NMR 162.0, 160.4, 140.0, 116.1, 108.1, 103.4, 21.1; IR (KBr): 3144, 3097, 2979, 2833, 2227, 1652, 1635, 1616, 1539, 1484, 1242, 1218, 1173, 819 cm⁻¹; Mass spectrum m/z: 134, 105, 78, 63, 51; Purity: 98.8% by HPLC analysis (peak area basis).

(c) Preparation of 2-Chloro-3-Cyano-4-Methylpyridine (Chlorination)

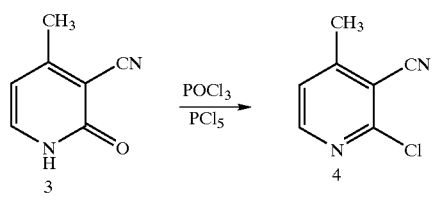

The product of the preceding step, 4-methyl-3-cyano-2-pyridone (40.7 g, 0.304 moles) was added to a stirred solution of POCL₃ (140 g, 0.912 moles) and PCl₅ (19.0 g, 0.091 moles). The reaction was heated to reflux (approximately 115° C.) and held under those conditions for two hours. Excess POCL₃ was removed by distillation. The reaction mixture was then cooled followed by the addition of water (30 mL) water. The aqueous mixture was extracted with 30 mL methylene chloride. The extracts were concentrated and 43.2 g was recovered as a tan solid, which was determined to be 2-chloro-3-cyano-4-methylpyridine.

mp: 102–104° C. Yield: 98.2%; ¹H NMR: 8.03 (d, J=2 Hz, 1H), 7.6 (d, J=2 Hz, 1H), 2.5 (s, 3H); ¹³C NMR 156.1, 152.6, 151.8, 124.9, 114.4, 111.8, 20.6; Mass spectrum m/z: 155, 154, 152, 117, 116, 90, 89, 76, 64, 63, 62; FTIR (KBr): 3144, 2979, 2834, 2228, 1653, 1616, 1540, 1484, 1242, 1218, 1173, 819, 607 cm⁻¹; Purity: 98.6% by HPLC analysis (peak area basis).

(d) Preparation of 2-Chloro-3-amido-4-methylpyridine (Addition of Water)

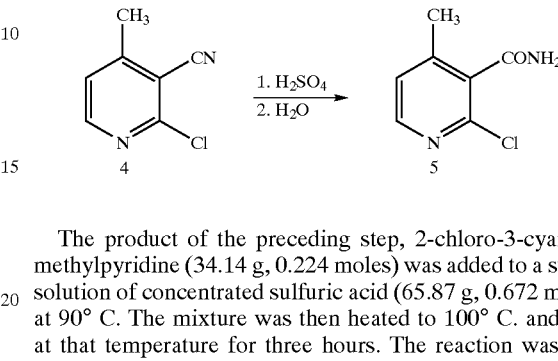

The product of the preceding step, 2-chloro-3-cyano-4-methylpyridine (34.14 g, 0.224 moles) was added to a stirred solution of concentrated sulfuric acid (65.87 g, 0.672 moles) at 90° C. The mixture was then heated to 100° C. and held at that temperature for three hours. The reaction was then cooled to 90° C. followed by the addition of water (121 mL). The mixture was cooled to 10° C. and held at that temperature for one hour. The solid product was isolated from the reaction mixture by filtration, washed with water (16 mL) and dried at 70° C. under full vacuum to give 34.7 g of 2-chloro-3-amido-4-methylpyridine (5).

mp: 178–179° C.; Yield: 92.93%; ¹H NMR: 8.28 (d, J=8 Hz, 1H), 8.09 (s, 1H), 7.84 (s, 1H), 7.34 (d, J=8 Hz, 1H), 2.31 (s, 3H); ¹³C NMR: 166.4, 1149.0, 1437.8, 146.2, 136.0, 125.0, 18.9; Mass spectrum m/z: 155, 154, 152, 116, 91, 90, 89, 88, 76, 75, 64, 63, 62, 52, 51; FTIR (KBr): 3407, 3303, 3194, 3116, 3069, 3031, 2962, 2847, 1664, 1539, 1475, 1458, 1380, 1174, 1145, 798, 595 cm⁻¹.

(e) Preparation of 2-Chloro-3-amino-4-methylpyridine

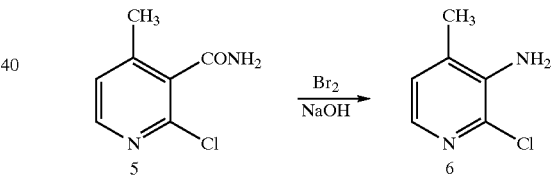

Bromine (34.7 g, 0.204 moles) was added to a stirred solution of sodium hydroxide (8.14 g. 0.224 moles) and water (205 mL) at 0° C. The product of the preceding step, 2-chloro-3-amido-4-picoline (34.7 g, 0.204 moles) was then added to the reaction mixture followed by heating to 22° C. An additional 66 mL water was then added to the reaction mixture followed by heating to 70° C. and stirring for one additional hour. The reaction mixture was cooled to ambient temperature and extracted with methylene chloride (60 mL). The methylene chloride was removed by rotary evaporation to give 24.8 g of 2-chloro-3-amino-4-methylpyridine (6).

mp: 69° C. Yield: 93.1%; ¹H NMR: 7.5 (d, J=4.64 Hz, 1H), 7.0 (d, J=4.28 Hz, 1H), 5.25 (s, 2H), 2.1 (s, 3H); ¹³C NMR: 140.0, 136.2, 135.6, 131.9, 125.7, 19.0; IR (KBr): 3429, 3308, 3198, 1630, 1590, 1550, 1475, 1451, 1441, 1418, 1377, 1295, 1122, 860, 821, 656, 527 cm⁻¹; Mass spectrum m/z: 145, 144, 142, 107, 106, 105, 80, 79, 78, 62, 54, 53, 52; Purity: 100.2%, HPLC analysis (peak area basis).

What is claimed is:

1. A process for preparing 2-chloro-3-amino-4-methylpyridine

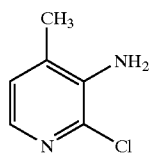

which comprises the following steps:
  (a) reacting acetylacetaldehyde dimethyl acetal with malononitrile, in the presence of an ammonium salt catalyst, to yield a mixture of 4,4-dicyano-3-methyl-3-butenal dimethyl acetal and 1,1-dicyano-4-methoxy-2-methyl-1,3-butadiene,
  (b) treating the mixture of 4,4-dicyano-3-methyl-3-butenal dimethyl acetal and 1,1-dicyano-4-methoxy-2-methyl-1,3-butadiene so produced with a strong acid and water, to yield 3-cyano-4-methyl-2-pyridone,
  (c) treating the 3-cyano-4-methyl-2-pyridone so produced with a strong chlorinating agent, to yield 3-cyano-2-chloro-4-methylpyridine
  (d) treating the 3-cyano-2-chloro-4-methylpyridine produced in the preceding step with a strong acid and water, to yield 2-chloro-3-amido-4-methylpyridine, and
  (e) treating the 2-chloro-3-amido-4-methylpyridine produced in the preceding step with a strong base and a halide, to yield 2-chloro-3-amino-4-methylpyridine.

2. The process of claim 1 wherein the ammonium salt catalyst used in step (a) is piperidinium acetate.

3. The process of claim 1 wherein the acid used in step (b) is sulfuric acid.

4. The process of claim 1 wherein the chorinating agent used in step (c) is a mixture of $POCL_3$ and $PCl_5$.

5. The process of claim 1 wherein the strong acid used in step (d) is sulfuric acid.

6. The process of claim 1 wherein the base and halide used in step (e) are, respectively, NaOH and $Br_2$.

7. The process of claim 1 wherein the crude mixture of 4,4-dicyano-3-methyl-3-butenal dimethyl acetal and 1,1-dicyano-4-methoxy-2-methyl-1,3-butadiene produced in step (a) is washed with water to remove catalyst, followed by evaporation to remove solvent, and the remaining crude mixture is then subjected to distillation, to remove high boiling reaction byproducts, and then the remaining process steps (b) though (e) are carried out.

8. The process of claim 7, wherein the distillation is continuous, short path distillation.

9. The process of claim 8 wherein the distillation is accomplished via wiped or thin film evaporation.

10. 4,4-Dicyano-3-methyl-3-butenal dimethyl acetal.

11. 1,1-Dicyano-4-methoxy-2-methyl-1,3-butadiene.

* * * * *